United States Patent [19]

Switzer

[11] Patent Number: 5,596,091
[45] Date of Patent: Jan. 21, 1997

[54] ANTISENSE OLIGONUCLEOTIDES COMPRISING 5-AMINOALKYL PYRIMIDINE NUCLEOTIDES

[75] Inventor: Christopher Switzer, Moreno Valley, Calif.

[73] Assignee: The Regents of the University of California, Oakland, Calif.

[21] Appl. No.: 214,603

[22] Filed: Mar. 18, 1994

[51] Int. Cl.$^6$ .............. C07H 21/04; C12Q 1/68; C12P 19/34
[52] U.S. Cl. ............ 536/24.5; 536/23.1; 536/24.1; 536/24.3; 435/6; 435/911
[58] Field of Search .............. 536/24.1, 23.1, 536/24.3, 24.5; 435/6, 91.1

[56] References Cited

U.S. PATENT DOCUMENTS

| | | | |
|---|---|---|---|
| 4,469,863 | 9/1984 | Ts'o et al. | 536/24.5 |
| 4,757,055 | 7/1988 | Miller et al. | 514/44 |
| 5,264,423 | 11/1993 | Cohen et al. | 514/44 |
| 5,276,019 | 1/1994 | Cohen et al. | 514/44 |

FOREIGN PATENT DOCUMENTS

WO93/15742  8/1993  WIPO.

OTHER PUBLICATIONS

Bodnar (1983) "Effect of nucleotide analogs on the cleavage of DNA by the restriction enzymes etc." J. Biol. Chem 258:15206–15213.

Miller et al, Nucleic Acids Research 13, 2559–2568 (1985).
Allen et al, Biochemistry 28, 4601–4607 (1989).
Kropinski et al, Biochemistry 12, 151–157 (1973).
Stirchak, et al. (1987) "Uncharged Steroregular Nucleic Acid Analogues. 1. Synthesis of a Cytosine–Containing Oligomer with Carbamate Internucleoside Linkages," *J. Org. Chem.*, 52(19):4202–4206.
Cormier, et al. (1988) "Synthesis of hexanucleotide analogues containing diisopropylsilyl internucleotide linkages," *Nucleic Acids Research*, 16(10:4583.
Uhlman, Eugen, et al. (1990) "Antisense Oligonucleotides: A New Therapeutic Principle," *Chemical Reviews*, 90:543–584.
Hashimoto, Hiromasa, et al. (1993), "Formation of Chimeric Duplexes between Zwitterionic and Natural DNA," *J. Org. Chem.*, 58:4194–4195.
Hashimoto, Hiromasa, et al. (1993), "Zitterionic DNA," *J. Am. Chem. Soc.* 115:7128–7134.

Primary Examiner—John L. Leguyader
Assistant Examiner—Scott D. Priebe
Attorney, Agent, or Firm—Townsend and Townsend and Crew LLP

[57] ABSTRACT

Replacement of the natural nucleotides with unnatural zwitterionic nucleotides having a cationic moiety tethered to the base (or analog thereof) results in oligodeoxynucleotides with diminished charge but undiminished ability to complex with DNA at low ionic strengths. We have now discovered that DNA can be made fully zwitterionic by introducing tethered cationic moieties to the bases without affecting duplex formation. The resulting oligonucleotides have the further advantages of being nuclease resistant.

3 Claims, No Drawings

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligodeoxynucleotide"

( i x ) FEATURE:
        ( A ) NAME/KEY: modified_base
        ( B ) LOCATION: 6
        ( D ) OTHER INFORMATION: /mod_base=OTHER
            / note="Zwitterionic monomer 1."

( i x ) FEATURE:
        ( A ) NAME/KEY: modified_base
        ( B ) LOCATION: 8
        ( D ) OTHER INFORMATION: /mod_base=OTHER
            / note="Zwitterionic monomer 1"

( i x ) FEATURE:
        ( A ) NAME/KEY: modified_base
        ( B ) LOCATION: 10
        ( D ) OTHER INFORMATION: /mod_base=OTHER
            / note="Zwitterionic monomer 1."

( i x ) FEATURE:
        ( A ) NAME/KEY: modified_base
        ( B ) LOCATION: 12
        ( D ) OTHER INFORMATION: /mod_base=OTHER
            / note="Zwitterionic monomer 1."

( x i ) SEQUENCE DESCRIPTION: SEQ ID NO:1:

TTTTTTTTT TT                                            1 2

( 2 ) INFORMATION FOR SEQ ID NO:2:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligodeoxynucleotide"

( i x ) FEATURE:
        ( A ) NAME/KEY: modified_base
        ( B ) LOCATION: 2..12
        ( D ) OTHER INFORMATION: /mod_base=OTHER
            / note="Zwitterionic monomer 1 at each position designated."

( x i ) SEQUENCE DESCRIPTION: SEQ ID NO:2:

TTTTTTTTT TT                                                        1 2

( 2 ) INFORMATION FOR SEQ ID NO:3:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligodeoxynucleotide"

( i x ) FEATURE:
        ( A ) NAME/KEY: modified_base
        ( B ) LOCATION: 6
        ( D ) OTHER INFORMATION: /mod_base=OTHER
            / note="Zwitterionic monomer 2."

( i x ) FEATURE:
        ( A ) NAME/KEY: modified_base
        ( B ) LOCATION: 8
        ( D ) OTHER INFORMATION: /mod_base=OTHER
            / note="Zwitterionic monomer 2."

( i x ) FEATURE:
        ( A ) NAME/KEY: modified_base
        ( B ) LOCATION: 10
        ( D ) OTHER INFORMATION: /mod_base=OTHER
            / note="Zwitterionic monomer 2."

( i x ) FEATURE:
        ( A ) NAME/KEY: modified_base
        ( B ) LOCATION: 12
        ( D ) OTHER INFORMATION: /mod_base=OTHER
            / note="Zwitterionic monomer 2."

( x i ) SEQUENCE DESCRIPTION: SEQ ID NO:3:

TTTTTTTTT TT                                                        1 2

( 2 ) INFORMATION FOR SEQ ID NO:4:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligodeoxynucleotide"

( i x ) FEATURE:
        ( A ) NAME/KEY: modified_base
        ( B ) LOCATION: 2
        ( D ) OTHER INFORMATION: /mod_base=OTHER / note="Zwitterionic monomer 1."

(ix) FEATURE:
    (A) NAME/KEY: modified_base
    (B) LOCATION: 4
    (D) OTHER INFORMATION: /mod_base=OTHER
        / note="Zwitterionic monomer 1."

(ix) FEATURE:
    (A) NAME/KEY: modified_base
    (B) LOCATION: 6
    (D) OTHER INFORMATION: /mod_base=OTHER
        / note="Zwitterionic monomer 1."

(ix) FEATURE:
    (A) NAME/KEY: modified_base
    (B) LOCATION: 8
    (D) OTHER INFORMATION: /mod_base=OTHER
        / note="Zwitterionic monomer 1."

(xi) SEQUENCE DESCRIPTION: SEQ ID NO:4:

CTTTCTCTCC CT                                  12

(2) INFORMATION FOR SEQ ID NO:5:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc ="Oligodeoxynucleotide"

(ix) FEATURE:
    (A) NAME/KEY: modified_base
    (B) LOCATION: 5
    (D) OTHER INFORMATION: /mod_base=OTHER
        / note="Zwitterionic monomer 3."

(ix) FEATURE:
    (A) NAME/KEY: modified_base
    (B) LOCATION: 7
    (D) OTHER INFORMATION: /mod_base=OTHER
        / note="Zwitterionic monomer 3."

(ix) FEATURE:
    (A) NAME/KEY: modified_base
    (B) LOCATION: 9
    (D) OTHER INFORMATION: /mod_base=OTHER
        / note="Zwitterionic monomer 3."

(ix) FEATURE:
    (A) NAME/KEY: modified_base
    (B) LOCATION: 11
    (D) OTHER INFORMATION: /mod_base=OTHER
        / note="Zwitterionic monomer 3."

(xi) SEQUENCE DESCRIPTION: SEQ ID NO:5:

CTTTCTCTCC CT                                  12

(2) INFORMATION FOR SEQ ID NO:6:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc ="Oligodeoxynucleotide"

(ix) FEATURE:
    (A) NAME/KEY: modified_base
    (B) LOCATION: 2..12
    (D) OTHER INFORMATION: /mod_base=OTHER / note="Zwitterionic monomer 1 at each position
designated."

( x i ) SEQUENCE DESCRIPTION: SEQ ID NO:6:

CTTTCTCTCC CT                                                                                              12

( 2 ) INFORMATION FOR SEQ ID NO:7:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligodeoxynucleotide"

( x i ) SEQUENCE DESCRIPTION: SEQ ID NO:7:

CTTTCTCTCC CT                                                                                              12

( 2 ) INFORMATION FOR SEQ ID NO:8:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligodeoxynucleotide"

( x i ) SEQUENCE DESCRIPTION: SEQ ID NO:8:

TTTTTTTTTT TT                                                                                              12

( 2 ) INFORMATION FOR SEQ ID NO:9:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligodeoxynucleotide"

( x i ) SEQUENCE DESCRIPTION: SEQ ID NO:9:

AAAAAAAAAA AA                                                                                              12

( 2 ) INFORMATION FOR SEQ ID NO:10:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligodeoxynucleotide"

( x i ) SEQUENCE DESCRIPTION: SEQ ID NO:10:

AGGGAGAGAA AG                                                                                              12

( 2 ) INFORMATION FOR SEQ ID NO:11:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: other nucleic acid
( A ) DESCRIPTION: /desc ="Oligodeoxynucleotide"

( x i ) SEQUENCE DESCRIPTION: SEQ ID NO:11:

AAAAGAAAAA AA                12

( 2 ) INFORMATION FOR SEQ ID NO:12:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="Oligodeoxynucleotide"

( x i ) SEQUENCE DESCRIPTION: SEQ ID NO:12:

AGGGAGGGAA AG                12

( 2 ) INFORMATION FOR SEQ ID NO:13:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="Oligodeoxynucleotide"

( x i ) SEQUENCE DESCRIPTION: SEQ ID NO:13:

AGGGAAAGAA AG                12

ANTISENSE OLIGONUCLEOTIDES COMPRISING 5-AMINOALKYL PYRIMIDINE NUCLEOTIDES

The present invention relates to novel antisense oligonucleotides derived from zwitterionic monomers. These oligonucleotides are capable of forming duplexes with natural DNA which are resistant to nuclease degradation and are useful in diagnostic and therapeutic applications.

This invention was made with Government support under Grant No. GM47375-01, awarded by the National Institutes of Health. The Government has certain rights in this invention.

BACKGROUND OF THE INVENTION

Antisense oligonucleotides are synthetic oligonucleotides which are designed to bind to RNA by Watson-Crick base pairing. This binding, or hybridization can result in the selective inhibition of mRNA expression. Additionally, the antisense oligonucleotides may block gene expression by inhibition of replication or transcription of DNA by Hoogsteen bonding. This type of bonding results in the formation of a triple helix wherein the oligonucleotide analog binds in a sequence-specific manner in the major groove of the DNA duplex structure. A number of cellular processes can be inhibited depending on where the oligonucleotide hybridizes on regions of DNA or mRNA. To be effective as therapeutic agents, oligonucleotides must reach the interior of target cells unaltered. This requires the oligonucleotides to be able to penetrate the cell membrane and to be resistant to intra- and extracellular nucleases. Additionally, antisense oligonucleotides can be used for diagnostic purposes by coupling the oligonucleotide to a suitable imaging agent (i.e., radiolabel, fluorescent tag, or biotin) or solid support.

Natural oligonucleotides are negatively charged and do not easily penetrate the cell membrane. Additionally, they are susceptible to degradation by nucleases which cleave the phosphodiester linkage. For these reasons, efforts to prepare pharmaceutically active oligonucleotides have focused on synthetic analogs which address these problems.

A number of strategies have been employed in the preparation of antisense oligonucleotides including, replacement of one non-bridging oxygen in phosphodiester linkages with sulfur (see, Cohen, et al., U.S. Pat. Nos. 5,264,423 and 5,276,019); replacement of both non-bridging oxygens in the phosphodiester linkages with sulfur (see, Brill, et al., *J. Am. Chem. Soc.* 111:2321 (1989)); use of nonionic alkyl and aryl phosphonates in place of the phosphate linking group (see, Miller, et al., U.S. Pat. Nos. 4,469,863 and 4,757,055); and, replacement of phosphorus atoms with carbon or silicon (see, Stirchak, et al., *J. Org. Chem.* 52:4202–4206 (1987) and Cormier, et al., *Nucleic Acids Res.* 16:4583 (1988), respectively). These strategies and related efforts are the subject of a recent review (see, Uhlmann, et al., *Chem. Reviews* 90:543–584 (1990)).

More recently, others have focused on the preparation of charge-neutral antisense oligonucleotides which have zwitterionic moieties attached to the phosphodiester backbone (see, Cook, WO 93/15742 (1993)).

Base modification has been virtually ignored as a method by which to engineer oligonucleotides for use as antisense agents. However, nature has employed a design strategy of attaching a positively charged species to a thymidine base. Thus, bacteriophage φW-14 is known to replace approximately half of the thymines present in its DNA with positively charged α-putrescinylthymine. This results in approximately one hypermodified base every eight nucleotides on average. These and other hypermodified bacteriophage DNAs have been shown to resist a variety of endonucleases and some exonucleases as well. While it is known from these and other examples that the DNA major groove will tolerate some substitution without a significant deleterious effect on duplex formation, little information is available about the effect of introducing contiguous, bulky, charged modifying groups into the major groove.

SUMMARY OF THE INVENTION

We have discovered that modified oligonucleotides can be prepared in substantially pure form having diminished charge but undiminished ability to complex with natural DNA at low ionic strengths. These modified oligonucleotides are prepared by replacing natural nucleotides with unnatural zwitterionic nucleotides having a cationic moiety tethered to the base. The modified oligonucleotides have the advantages of being membrane permeable and nuclease resistant, and can further form duplexes even when completely zwitterionic. As a result, the modified oligonucleotides of the present invention may be used in various applications such as where antisense therapy is desired, they may be coupled with an imaging agent for use in diagnostic applications, or they may be used in in vitro hybridization assays where nuclease resistant capture probes or signal probes are desired.

DETAILED DESCRIPTION

Abbreviations and Definitions

The following abbreviations are used herein: Bz, benzoyl; CPG, controlled pore glass; DCC, dicyclohexylcarbodiimide; DMF, dimethylformamide; DMSO, dimethylsulfoxide; DMT, dimethoxytrityl; EDTA, ethylenediaminetetraacetic acid; FAB, fast atom bombardment; HPLC, high performance liquid chromatography; HRMS, high resolution mass spectrometry; IR, infrared spectrometry; NMR, nuclear magnetic resonance spectrometry; PAGE, polyacrylamide gel electrophoresis; PEG, polyethylene glycol; TBDMS, tert-butyldimethylsilyl; TEAA, triethylammonium acetate; and TLC, thin layer chromatography.

As used herein the term "natural DNA" refers to oligomers composed only of the naturally occuring nucleotides. The oligomers may be either single- or double-stranded.

The term "oligonucleotide" refers to a single or double-stranded polymer of deoxyribonucleotide or ribonucleotide bases read from the 5' to the 3' end. It includes both self-replicating plasmids, infectious polymers of DNA or RNA and non-functional DNA or RNA. The term "modified oligonucleotides" refers to those nucleotides having one or more nucleotides replaced by zwitterionic nucleotides.

The term "complementary" means that one nucleic acid hybridizes selectively to, another nucleic acid. Selectivity of hybridization exists when hybridization (or base pairing) occurs that is more selective than total lack of specificity. Typically, selective hybridization will occur when there is at least about 55% paired bases over a stretch of at least 14–25 nucleotides, preferably at least about 65%, more preferably at least about 75%, and most preferably at least about 90%. See, M. Kanehisa *Nucleic Acids Res.* 12:203 (1984), incorporated herein by reference.

As used herein, the term "alkyl" refers to a saturated hydrocarbon radical which may be straight-chain or branched-chain (for example, ethyl, isopropyl, t-amyl, or 2,5-dimethylhexyl). When "alkyl" is used to refer to a linking group, it is taken to be a group having two available valences for covalent attachment, for example, —CH$_2$CH$_2$—, —CH$_2$CH$_2$CH$_2$—, —CH$_2$CH$_2$CH(CH$_3$)CH$_2$— and —CH$_2$(CH$_2$CH$_2$)$_2$CH$_2$—. Preferred alkyl groups as substituents are those containing 1 to 10 carbon atoms, with those containing 1 to 6 carbon atoms being particularly preferred. Preferred alkyl groups as linking groups are those containing 1 to 10 carbon atoms, with those containing 3 to 6 carbon atoms being particularly preferred. The term "unsaturated alkyl" refers to alkyl groups having one or more double bonds or triple bonds. When "unsaturated alkyl" is used to refer to a linking group, it is taken to be a group having two available valences for covalent attachment, for example, —CH=CHCH$_2$—, —C≡CCH$_2$—, —CH$_2$CH=C(CH$_3$)CH$_2$— and —C≡C—(CH$_2$CH$_2$)$_2$CH$_2$—.

The terms "dialkyl ether" and "dialkylthioether" when used to refer to linking groups refers to such radicals as —CH$_2$OCH$_2$—, —CH$_2$OCH$_2$CH$_2$—, —CH$_2$CH$_2$CH$_2$OCH$_2$—, —CH$_2$CH$_2$OCH$_2$CH$_2$—, —CH$_2$SCH$_2$—, —CH$_2$SCH$_2$CH$_2$—, —CH$_2$CH$_2$CH$_2$SCH$_2$— and —CH$_2$CH$_2$SCH$_2$CH$_2$—, and their branched-chain counterparts.

The term "cationic moiety" refers to a group which carries a positive charge, for example, ammonium, mono-, di- or trialkylammonium, dialkylsulfonium and trialkylphosphonium.

The term "effective binding amount," refers to an amount of modified oligonucleotides sufficient to form a duplex with a target oligonucleotide and either elicit a desired therapeutic response or, when the modified oligonucleotide is coupled with an imaging agent, provide sufficient signal for diagnostic purposes.

The term "chimeric duplex" refers to duplex DNA which is formed from one strand of natural DNA and a modified oligonucleotide.

As used herein, all numerical ranges are meant to be inclusive of their upper and lower limits.

DESCRIPTION OF THE INVENTION

In one aspect, the present invention provides modified oligonucleotides of formula I.

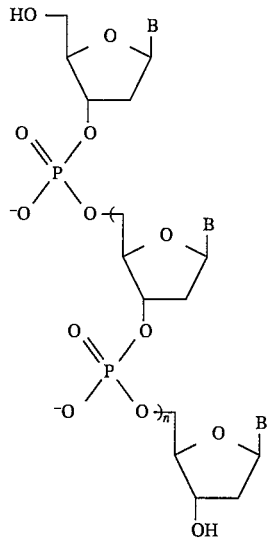

In this formula, n is an integer from 4 to 30, inclusive of the upper and lower limits. Preferably, n is an integer of from 4 to 15

The symbol B represents a variety of structures which may be the same or different within each oligonucleotide. Some of these structures are represented by formulas II–V:

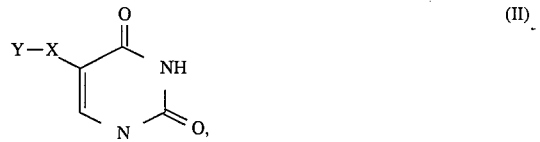

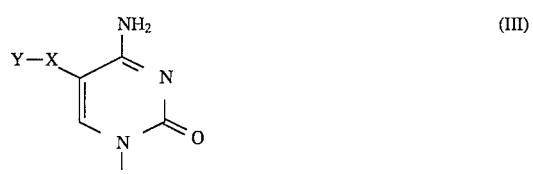

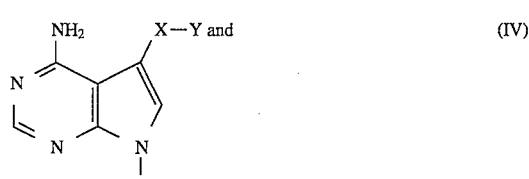

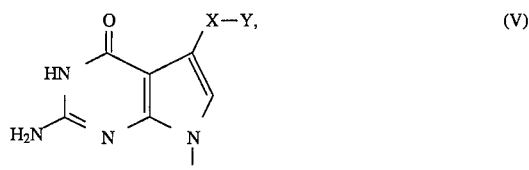

in which X is a linking group which is $C_1$–$C_{10}$ alkyl, $C_1$–$C_{10}$ unsaturated alkyl, dialkyl ether or dialkylthioether; and each Y may be the same or different and is a cationic moiety which is —(NH$_3$)$^+$, —(NH$_2$R$^1$)$^+$, —(NHR$^1$R$^2$)$^+$, —(NR$^1$R$^2$R$^3$)$^+$, dialkylsulfonium or trialkylphosphonium; and R$^1$, R$^2$, and R$^3$ are each independently lower alkyl having from one to ten carbon atoms. Preferred linking groups for X are $C_1$–$C_{10}$ alkyl and $C_1$–$C_{10}$ unsaturated alkyl. Particularly preferred linking groups for X are $C_3$–$C_6$ alkyl and $C_3$–$C_6$ unsaturated alkyl. Preferred groups for Y are —(NH$_3$)$^+$, —(NH$_2$R$^1$)$^+$, —(NHR$^1$R$^2$)$^+$, —(NR$^1$R$^2$R$^3$)$^+$, with —(NH$_3$)$^+$ being particularly preferred.

Other groups for B include adenine (A), guanine (G), thymine (T) and cytosine (C), with the provision that when n is from 4 to 8, no more than 30% of Bs are A, G, C or T, and when n is from 9 to 30, no more than 50% of Bs are A, G, C or T. Preferred groups for B include formulas II and III, and A, G, C and T.

Another aspect of the present invention resides in compositions for binding to an RNA, a DNA, a protein or a peptide. These compositions contain a modified oligonucleotide of the present invention which is present in an effective amount for binding to RNA, DNA, a protein or a peptide, along with an acceptable sterile pharmaceutical carrier.

Still another aspect of the present invention resides in a method for forming chimeric duplexes and triplexes between zwitterionic oligonucleotides and natural DNA. In this method, natural DNA is treated with a complementary modified oligonucleotide of formula I.

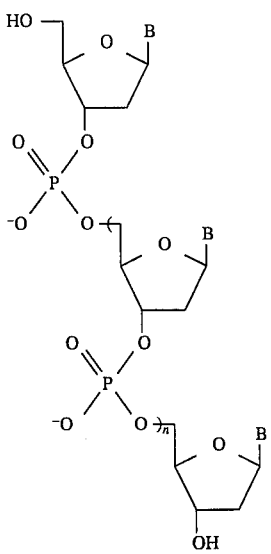

In this formula, n is an integer from 4 to 30 and preferably, n is an integer of from 4 to 15.

The symbol B represents a variety of structures which may be the same or different within each oligonucleotide. Some of these structures are represented by formulas II–V:

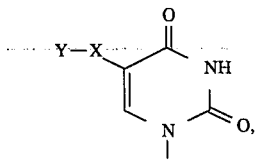

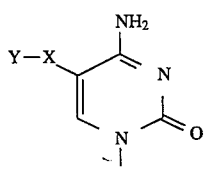

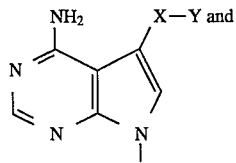

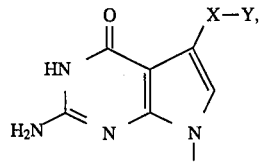

in which X is a linking group which is $C_1$–$C_{10}$ alkyl, $C_1$–$C_{10}$ unsaturated alkyl, dialkyl ether or dialkylthioether; and each Y may be the same or different and is a cationic moiety which is —$(NH_3)^+$, —$(NH_2R^1)^+$, —$(NHR^1R^2)^+$, —$(NR^1R^2R^3)^+$, dialkylsulfonium or trialkylphosphonium; and $R^1$, $R^2$, and $R^3$ are each independently lower alkyl having from one to ten carbon atoms. Preferred linking groups for X are $C_1$–$C_{10}$ alkyl and $C_1$–$C_{10}$ unsaturated alkyl. Particularly preferred linking groups for X are $C_3$–$C_6$ alkyl and $C_3$–$C_6$ unsaturated alkyl. Preferred groups for Y are —$(NH_3)^+$, —$(NH_2R^1)^+$, —$(NHR^1R^2)^+$, —$(NR^1R^2R^3)^+$, with —$(NH_3)^+$ being particularly preferred.

Other groups for B include adenine (A), guanine (G), thymine (T) and cytosine (C), with the provision that when n is from 4 to 8, no more than 30% of Bs are A, G, C or T, and when n is from 9 to 30, no more than 50% of Bs are A, G, C or T. Preferred groups for B include formulas II and III, and A, G, C and T.

In all aspects of the present invention, preferred positions for the zwitterionic nucleotide monomers are near or at the 5'- and 3'-termini of the modified oligonucleotide.

The modified oligonucleotides used in the present invention may be prepared from naturally occurring nucleotides and zwitterionic nucleotides, using conventional techniques. Some preferred zwitterionic nucleotides can be prepared using synthetic methods known to one of skill in the art and described in Hashimoto, et al., *J. Org. Chem.* 58:4194–4195 (1993) and Hashimoto, et al., *J. Am. Chem. Soc.* 115:7128–7134 (1993), incorporated herein by reference. Briefly, zwitterionic uridine and cytidine analogs are synthesized as their phosphoramidite esters beginning with the corresponding 5-iodo-2'-deoxyuridine and 5-iodo-2'-deoxycytidine. Reaction of the iodo-nucleosides with an appropriately protected amino alkyne in the presence of a palladium catalyst provides the desired carbon framework for further elaboration. Hydrogenation of the newly introduced alkyne can be accomplished over a palladium on carbon catalyst to provide analogs having a protected amine which is linked to the nucleotide via a saturated carbon tether. In other embodiments the alkyne may kept as part of the linking group or may be reduced to an alkene using controlled hydrogenation over palladium on carbon catalysts. The remaining steps to the phosphoramidite esters involve the addition of various protecting groups which are selected for their compatibility with subsequent oligonucleotide synthesis. Such protecting groups are well known to one of skill in the art and conditions and references for particular procedures are found in Greene and Wuts, *Protecting Groups in Organic Synthesis*, Wiley-Interscience, Second Edition, (1991), incorporated herein by reference.

The oligonucleotides of the present invention may be synthesized in solid phase or in solution. Generally, solid phase synthesis is preferred. Detailed descriptions of the procedures for solid phase synthesis of oligonucleotides by phosphite-triester, phosphotriester, and H-phosphonate chemistries are widely available. See, for example, Itakura, U.S. Pat. No. 4,401,796; Caruthers, et al., U.S. Pat. Nos. 4,458,066 and 4,500,707; Beaucage, et al., *Tetrahedron Lett.*, 22:1859–1862 (1981); Matteucci, et al., *J. Am. Chem. Soc.*, 103:3185–3191 (1981); Caruthers, et al., *Genetic Engineering*, 4:1–17 (1982); Jones, chapter 2, Atkinson, et al., chapter 3, and Sproat, et al., chapter 4, in *Oligonucleotide Synthesis: A Practical Approach*, Gait (ed.), IRL Press, Washington D.C. (1984); Froehler, et al., *Tetrahedron Lett.*, 27:469–472 (1986); Froehler, et al., *Nucleic Acids Res.*, 14:5399–5407 (1986); Sinha, et al. *Tetrahedron Lett.*, 24:5843–5846 (1983); and Sinha, et al., *Nucl. Acids Res.*, 12:4539–4557 (1984) which are incorporated herein by reference.

Generally, the timing of delivery and concentration of zwitterionic monomeric nucleotides utilized in a coupling cycle will not differ from the protocols typical for unmodified commercial phosphoramidites used in commercial DNA synthesizers. In these cases, one may merely add the solution containing the protected zwitterionic monomers to a receptacle on a port provided for an extra phosphoramidite on a commercial synthesizer (e.g., model 380B, Applied Biosystems, Foster City, Calif., U.S.A.). However, where the coupling efficiency of a particular protected zwitterionic monomer is substantially lower than the other phosphoramidites, it may be necessary to alter the timing of delivery or the concentration of the reagent in order to optimize the synthesis. Means of optimizing oligonucleotide synthesis protocols to correct for low coupling efficiencies are well known to those of skill in the art. Generally one merely increases the concentration of the reagent or the amount of the reagent delivered to achieve a higher coupling efficiency. Methods of determining coupling efficiency are also well known. For example, where the 5'-hydroxyl protecting group is dimethoxytrityl (DMT), coupling efficiency may be determined by measuring the DMT cation concentration during the acidic removal of the DMT group. DMT cation concentration is usually determined by spectrophotometrically monitoring the acid wash. The acid/DMT solution is a bright orange color. Alternatively, since capping prevents further extension of an oligonucleotide where coupling has failed, coupling efficiency may be estimated by comparing the ratio of truncated to full length oligonucleotides utilizing, for example, capillary electrophoresis or HPLC.

Solid phase oligonucleotide synthesis may be performed using a number of solid supports. A suitable support is one which provides a functional group for the attachment of a protected monomer which will become the 3' terminal base in the synthesized oligonucleotide. The support must be inert to the reagents utilized in the particular synthesis chemistry. Suitable supports are well known to those of skill in the art. Solid support materials include, but are not limited to polacryloylmorpholide, silica, controlled pore glass (CPG), polystyrene, polystyrene/latex, and carboxyl modified teflon. Preferred supports are amino-functionalized controlled pore glass and carboxyl-functionalized teflon.

Solid phase oligonucleotide synthesis requires, as a starting point, a fully protected monomer (e.g., a protected nucleoside) coupled to the solid support. This coupling is typically through the 3'-hydroxyl. Typically, a linker group is covalently bound to the 3'-hydroxyl on one end and covalently bound to the solid support on the other end. The first synthesis cycle then couples a nucleotide monomer, via its 3'-phosphate, to the 5'-hydroxyl of the bound nucleoside through a condensation reaction that forms a 3'-5' phosphodiester linkage. Subsequent synthesis cycles add nucleotide monomers to the 5'-hydroxyl of the last bound nucleotide. In this manner an oligonucleotide is synthesized in a 3' to 5' direction producing a "growing" oligonucleotide with its 3' terminus attached to the solid support.

Numerous means of linking nucleoside monomers to a solid support are known to those of skill in the art, although monomers covalently linked through a succinate or hemisuccinate to controlled pore glass are generally preferred. Conventional protected nucleosides coupled through a hemisuccinate to controlled pore glass are commercially available from a number of sources (e.g., Glen Research, Sterling, Vt., U.S.A.; Applied Biosystems, Foster City, Calif., U.S.A.; and Pharmacia LKB, Piscataway, N.J., U.S.A.).

Placement of a modified (protected zwitterionic) nucleotide at the 3' end of an oligonucleotide requires initiating oligonucleotide synthesis with a fully blocked furanosyl modified nucleotide linked to the solid support. In a preferred embodiment, linkage of the modified nucleoside is accomplished by first derivatizing the modified nucleotide as a hemisuccinate. The hemisuccinate may then be attached to amino functionalized controlled pore glass in a condensation reaction using mesitylene-2-sulfonyl chloride/1methyl-1H-imidazole as a condensing agent. Controlled pore glass functionalized with a number of different reactive groups is commercially available (e.g., Sigma Chemical, St. Louis, Mo., U.S.A.). A similar coupling scheme is described by Atkinson, et al., chapter 3 in *Oligonucleotide Synthesis: A Practical Approach,* Gait (ed.), IRL Press, Washington, D.C., (1984). Triisopropylbenzenesulfonyl chloride, imidazolides, triazolides or even the tetrazolides may also be used as condensing agent. Dicyclohexylcarbodiimide (DCC) and structural analogs are also suitable linkers. Other linkers and appropriate condensing groups are well known to those of skill in the art.

Once the full length oligonucleotide is synthesized, the oligonucleotide is deprotected and cleaved from the solid support prior to use. Cleavage and deprotection may occur simultaneously or sequentially in any order. The two procedures may be interspersed so that some protecting groups are removed from the oligonucleotide before it is cleaved off the solid support and other groups are deprotected from the cleaved oligonucleotide in solution. The sequence of events depends on the particular blocking groups present, the particular linkage to a solid support, and the preferences of the individuals performing the synthesis. Where deprotection precedes cleavage, the protecting groups may be washed away from the oligonucleotide which remains bound on the solid support. Conversely, where deprotection follows cleavage, the removed protecting groups will remain in solution with the oligonucleotide. Often the oligonucleotide will require isolation from these protecting groups prior to use.

In a preferred embodiment, and most commercial DNA syntheses, the protecting group on the 5'-hydroxyl is removed at the last stage of synthesis. The oligonucleotide is then cleaved off the solid support, and the remaining deprotection occurs in solution. Removal of the 5'-hydroxyl protecting group typically requires treatment with the same reagent utilized throughout the synthesis to remove the terminal 5'-hydroxyl groups prior to coupling the next nucleotide monomer. Where the 5'-hydroxyl protecting group is a dimethoxytrityl group, deprotection can be accomplished by treatment with acetic acid, dichloroacetic acid or trichloroacetic acid.

Typically, both cleavage and deprotection of the exocyclic amines are effected by first exposing the oligonucleotide attached to a solid phase support (via a base-labile bond) to the cleavage reagent for about 1–2 hours, so that the oligonucleotide is released from the solid support, and then heating the cleavage reagent containing the released oligonucleotide for at least 20–60 minutes at about 80°–90° C. so that the protecting groups attached to the exocyclic amines are removed. The deprotection step may alternatively take place at a lower temperature, but must be carried out for a longer period of time (e.g., the heating can be at 55° C. for 5 hours). In general, the preferred cleavage and deprotection reagent is concentrated ammonia.

Where the oligonucleotide is a ribonucleotide and the 2'-hydroxyl group is blocked with a tert-butyldimethylsilyl (TBDMS) moiety, the latter group may be removed using tetrabutylammonium fluoride in tetrahydrofuran at the end of synthesis. See Wu, et al., *J. Org. Chem.* 55:4717–4724 (1990). Phenoxyacetyl protecting groups can be removed with anhydrous ammonia in alcohol (under these conditions the TBDMS groups are stable and the oligonucleotide is not cleaved). The benzoyl protecting group of cytidine is also removed with anhydrous ammonia in alcohol.

Cleaved and fully deprotected oligonucleotides may be used directly (after lyophilization or evaporation to remove the deprotection reagent) in a number of applications, or they may be purified prior to use. Purification of synthetic oligonucleotides is generally desired to isolate the full length oligonucleotide from the protecting groups that were removed in the deprotection step and, more importantly, from the truncated oligonucleotides that were formed when oligonucleotides that failed to couple with the next nucleotide monomer were capped during synthesis.

Oligonucleotide purification techniques are well known to those of skill in the art. Methods include, but are not limited to, thin layer chromatography (TLC) on silica plates, gel electrophoresis, size fractionation (e.g., using a Sephadex column), reverse phase high performance liquid chromatography (HPLC) and anion exchange chromatography (e.g., using the mono-Q column, Pharmacia-LKB, Piscataway, N.J., U.S.A.). For a discussion of oligonucleotide purification see McLaughlin, et al., chapter 5, and Wu, et at., chapter 6 in *Oligonucleotide Synthesis: A Practical Approach,* Gait (ed.), IRL Press, Washington, D.C., (1984).

When the modified oligonucleotides of the present invention are to be used for imaging purposes, the desired label (e.g., radiolabel, fluorescent tag, biotin) can be attached by means well known to those of skill in the art and described in Telser, et al., *J. Am. Chem. Soc.* 111:7221–7226 and 7226–7232 (1989); Allen, et al., *Biochemistry* 28:4601–4607 (1989); Smith, et al., *Nucleic Acids Res* 13:2399–2412 (1985); Haralambidis, et al., ibid., 15:4857–4876 (1987); and Gebeyehu, et al., ibid., 15:4513–4535 (1987), the disclosures of which are incorporated herein by reference.

In preferred embodiments, the modified oligonucleotides of the present invention can be used to bind to DNA or RNA. The DNA or RNA sequences may be present in a variety of cells including normal cells, neoplastic cells, prokaryotic or eukaryotic cells, and a virus. The sequences may be bacterial sequences, plasmid sequences, viral sequences, chromosomal sequences, mitochondrial sequences, or plastid sequences. The target sequences may have both open reading frames for coding proteins and untranslated portions. The target sequences may therefore be involved in inhibiting the expression of a particular protein or enhancing the expression of a particular protein by inhibiting the expression of a repressor. Additionally, the target sequences may be involved in reducing the proliferation of viruses or neoplastic cells.

The modified oligonucleotides may be used in vitro or in vivo for modifying the phenotype of cells, or for limiting the proliferation of pathogens such as viruses, bacteria, protists, Mycoplasma species, Chlamydia or the like, or for inducing morbidity in neoplastic cells or specific classes of normal or diseased cells. Thus, the modified oligonucleotides may be administered to a host which is subject to or in a diseased state. When administered to a host, the oligonucleotides may be used to treat infection by a variety of pathogens, for example, enterotoxigenic bacteria, Pneumococci, Neisseria organisms, Giardia organisms, and Entamoebas. The modified oligonucleotides may also be used as cytotoxic or cytostatic agents for neoplastic cells, such as carcinoma cells, sarcoma cells, and lymphoma cells. The oligonucleotides may be used to modulate the function of immune system cells such as specific B-cells; specific T-cells, such as helper cells, suppressor cells, cytotoxic T-lymphocytes (CTL), and natural killer (NK) cells. Modulation of immune function can be useful in treatment of a variety of diseases such as cancer and immune system disease.

The modified oligonucleotides may be selected so as to be capable of interfering with transcription product maturation or expression of proteins by any of the mechanisms involved with the binding of the modified oligonucleotide to its target sequence. These mechanisms may include interference with processing, inhibition of transport across the nuclear membrane, cleavage by endonucleases, or the like.

The modified oligonucleotides may be complementary to nucleic acid sequences such as those encoding growth factors, lymphokines, immunoglobulins, T-cell receptor sites, MHC antigens, DNA or RNA polymerases, antibiotic resistance, multiple drug resistance (mdr), genes involved with metabolic processes, such as the formation of amino acids, nucleic acids, or the like. The modified oligonucleotides may be complementary to nucleic acid sequences including introns or flanking sequences associated with the open reading frames.

The modified oligonucleotides of the present invention may be used in the treatment of infectious diseases, cancers, autoimmune diseases and conditions associated with organ transplants. In the treatment of infectious diseases, the target sequences include those genes associated with AIDS, CMV, Herpes, drug resistance plasmids, and Trypanosomes. In the treatment of cancer, the target sequences can be DNA or RNA associated with oncogenes, tumor suppressor genes, and related genes. Additionally, the modified oligonucleotides may also target genes associated with drug resistance and their gene products. For the treatment of autoimmune diseases, the modified oligonucleotides can be, for example, target sequences associated with Rheumatoid arthritis, Type I diabetes, systemic lupus and multiple sclerosis.

In addition to binding nucleic acids, the modified oligonucleotides of the present invention may also be employed for binding to proteins including, but not limited to, ligands, receptors, and/or enzymes, whereby the modified oligonucleotides inhibit the activity of the proteins.

The modified oligonucleotides used in the present inventive method may be administered in any suitable manner, preferably with pharmaceutically acceptable carriers. One skilled in the art will appreciate that suitable methods of administering such compounds in the context of the present invention to an animal are available, and, although more than one route can be used to administer a particular compound, a particular route can provide a more immediate and more effective reaction than another route. Pharmaceutically acceptable carriers are also well-known to those who are skilled in the art. The choice of carrier will be determined in part by the particular modified oligonucleotide, as well as by the particular method used to administer the composition. Accordingly, there is a wide variety of suitable formulations of the pharmaceutical composition of the present invention.

Formulations suitable for oral administration can consist of (a) liquid solutions, such as an effective amount of the modified oligonucleotide dissolved in diluents, such as water, saline or PEG 400; (b) capsules, sachets or tablets, each containing a predetermined amount of the active ingredient, as solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium sterate, stearic acid, and other excipients, colorants, fillers, binders, diluents, buffering agents, mositening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such as carriers as are known in the art.

The active ingredient, alone or in combination with other suitable components, can be made into aerosol formulations to be administered via inhalation. These aerosol formulations can be placed into pressurized acceptable propellants, such as dichlorodifluoromethane, propane, nitrogen, and the like.

Suitable formulations for rectal administration include, for example, suppositories, which consist of the active ingredient with a suppository base. Suitable suppository bases include natural or synthetic triglycerides or paraffin hydrocarbons. In addition, it is also possible to use gelatin rectal capsules which consist of a combination of the active ingredient with a base, such as, for example, liquid triglycerides, polyethylene glycols, and paraffin hydrocarbons.

Formulations suitable for parenteral administration, such as, for example, by intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The dose administered to an animal, particularly a human, in the context of the present invention should be sufficient to effect a therapeutic response in the animal over a reasonable time frame. The dose will be determined by the strength of the particular compound employed and the condition of the animal, as well as the body weight or surface area of the animal to be treated. The size of the dose also will be determined by the existence, nature, and extent of any adverse side-effects that might accompany the administration of a particular compound in a particular animal.

In the practice of this invention, the modified oligonucleotides can be administered, for example, by intravenous infusion, orally, topically, intraperitoneally, intravesically or intrathecally.

Additionally, the modified oligonucleotides of the present invention may be administered encapsulated in liposomes, pharmaceutical compositions wherein the active ingredient is contained either dispersed or variously present in corpuscles consisting of aqueous concentric layers adherent to lipidic layers. The active ingredient, depending upon its solubility, may be present both in the aqueous layer and in the lipidic layer, or in what is generally termed a liposomic suspension. The hydrophobic layer, generally but not exclusively, comprises phospholipids such as lecithin and sphingomycelin, steroids such as cholesterol, more or less ionic surfactants such as dicetylphosphate, stearylamine, or phosphatidic acid, and/or other materials of a hydrophobic nature. The diameters of the liposomes generally range from about 15 nm to about 5 microns.

For oral administration, modified oligonucleotides of the present inventive method can be administered at the rate up to 3000 mg/m² body surface area, which approximates 6 grams/day in the average patient. A preferred rate is from 1 to 300 mg/m² body surface area. This can be accomplished via single or divided doses. For intravenous administration, such compounds can be administered at the rate of up to about 2500 mg/m²/d, preferably from about 0.1 to about 200 mg/m²/d. For intravesicle administration, such compounds can be administered at the rate of up to about 2500 mg/m²/d, preferably from about 0.1 to about 200 mg/m²/d. For topical administration, the rate can be up to about 2500 mg/m²/d, preferably from about 0.1 to about 200 mg/m²/d. The dose for inhalation/aerosol administration can be up to about 2500 mg/m²/d, preferably from about 0.1 to about 200 mg/m²/d. Direct intraperitoneal administration can be performed using up to about 3000 mg/m²/d, preferably from about 0.1 to about 100 mg/m²/d. The dose for reservoir administration to the brain or spinal fluid can be up to about 2000 mg/m²/d, preferably from about 0.1 to about 100 mg/m²/d. For slow release intraperitoneal or subcutaneous administration, the dose can be from about 0.1 to about 5000 mg/day in a bolus, preferably from about 1.0 to about 200 mg/day. For intrathecal administration, the dose can be up to about 2000 mg/m²/d, preferably from about 0.1 to about 100 mg/m²/d.

The following experimental results are offered by way of example and not by way of limitation.

EXAMPLES

General Methods

All air sensitive reactions were carried out under an atmosphere of $N_2$ or Ar. Melting points were taken on a Thomas-Hoover Uni-melt capillary melting point apparatus and are uncorrected. $^1H$ NMR spectra were recorded on a GE QE-300 (300 MHz) spectrometer. $^{13}C$ NMR spectra were recorded on either a GE QE-300 (75 MHz) or GN-500 (125 MHz) spectrometer. $^{31}P$ NMR spectra were recorded on a GE GN-500 (202 MHz, $H_3PO_4$ external standard) spectrometer. Infrared spectra were taken on a Nicolet 5-DX FT-IR spectrophotometer. Ultraviolet-visible spectra were recorded on a Hewlett-Packard 8452A diode-array spectrophotometer. Elemental analyses were carried out at Desert Analytics Organic Microanalysis Laboratory (Tucson, Ariz.). Mass spectra and exact mass determinations were recorded on a VG-ZAB-2FHF mass spectrometer using FAB ionization at the Southern California Regional Mass Spectrometry Facility (University of California, Riverside). Laser desorption mass spectra were recorded on a Finnegan Lasermat mass spectrometer at the Biotechnology Instrumentation Facility (University of California, Riverside). Chemicals were purchased from either Sigma or Aldrich Chemical Companies (St. Louis, Mo., USA and Milwaukee, Wis., USA, respectively). Solvents were purchased from Fisher Scientific. AG1X8 ($^-OH$) anion exchange resin was purchased from Bio-Rad (Hercules, Calif., USA). T4 polynucleotide kinase was purchased from Boehringer Mannheim (Indianapolis, Ind., USA). 5'-($\gamma$-$^{32}P$)ATP (~3000 Ci/mmol) was purchased from Amersham (Arlington Heights, Ill., USA). Controlled pore glass support was purchased from CPG, Inc. (Fairfield, N.J., USA). Tetrakis(triphenylphosphine)palladium (0) was prepared by a literature method. See, Coulson, D. R. *Inorganic Syntheses,* 13:121 (1971). Pyridine and $CH_2Cl_2$ were distilled from $CaH_2$ and stored over molecular sieves. Dimethylformamide (DMF) was stored over molecular sieves prior to use.

Two chemicals used in the following syntheses were prepared by methods well known in the art.

N-trifluoroacetyl-1-amino-5-hexyne

5-Hexyn-1-ol was treated with methanesulfonyl chloride in the presence of triethylamine and an organic solvent to provide the corresponding methanesulfonate ester. Displacement of the ester with the sodium salt of trifluoroacetamide (formed from NaH and trifluoroacetamide) provides N-trifluoroacetyl-1-amino-5-hexyne.

N-trifluoroacetyl-1-amino-2-propyne

Treatment of ethyl trifluoroacetate with 1-amino-2-propyne in a suitable organic solvent, produces N-trifluoroacetyl-1-amino-2-propyne after removal of solvent and distillation.

Synthesis

Examples 1–3 provide the syntheses of protected phosphoramidite precusors to the zwiterionic uridine analogs 1 and 2, and zwitterionic cytidine analog 3, respectively. Example 4 illustrates the methods used for oligonucleotide synthesis.

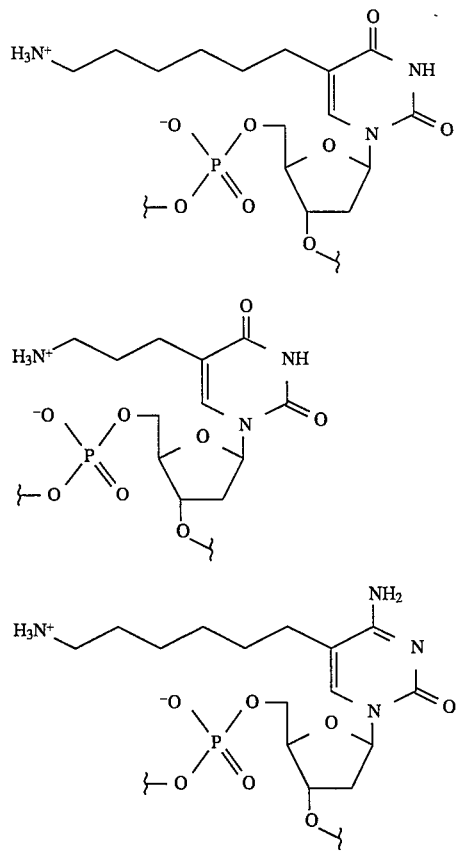

Example 1

This example illustrates the synthesis of 5-(6-N-(trifluoroacetyl)aminohexyl)-5'-O-(4,4'-dimethoxytrityl)-2'-deoxyuridine 2-cyanoethyl N,N-diisopropylphosphoramidite, (4) beginning with commercially available 5-iodo-2'-deoxyuridine.

A. Conversion of 5-iodo-2'-deoxyuridine to 5-(6-N-(trifluoroacetyl)-amino-1-hexynyl)-2'-deoxyuridine (5).

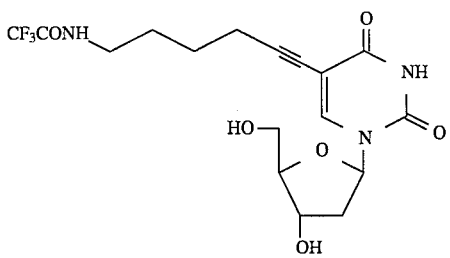

To a suspension of 5-iodo-2'-deoxyuridine (650 mg, 1.84 mmol) in $CH_2Cl_2$ (7.0 mL) was added trifluoroacetic anhydride (2.35 mL, 16.6 mmol) at room temperature. The mixture was stirred overnight. After concentration of the mixture, the residue was dried in vacuo at room temperature to give as a solid foam 1.30 g of 3',5'-di-O-trifluoroacetyl-5-iodo-2'-deoxyuridine.

To a mixture of di-O-trifluoroacetyl-5-iodo-2'-deoxyuridine, N-trifluoroacetyl-1-amino-5-hexyne (1.066 g, 5.52 mmol), tetrakis(triphenylphosphine)palladium (0) (150 mg, 0.13 mmol), and copper (I) iodide (50 mg, 0.26 mmol) were added dry DMF (10 mL) and $Et_3N$ (0.768 mL, 5.52 mmol). The mixture was stirred at room temperature for 24 h, and then concentrated under a vacuum. The residue was purified by flash chromatography ($SiO_2$, MeOH (5%–10%)/$CH_2Cl_2$). The fraction containing 5 was concentrated and treated with anion exchange resin AG1X8 ($HCO_3^-$, 1.58 g, 3.0 eq.) in 5 mL of 1/1, $CH_2Cl_2$/MeOH at room temperature for 30 min. Evaporation of the solvent gave 5: white solid, 605 mg, 78% yield; mp 154°–157° C. (MeOH/$Et_2O$); $^1H$ NMR (DMSO-d6) δ 1.48 (m, 2 H), 1.58 (m, 2 H), 2.10 (m, 2 H), 2.38 (t, 2 H, J=6.9 Hz), 3.20 (m, 2 H), 3.57 (m, 2 H), 3.77 (m, 1 H), 4.21 (m, 1 H), 5.08 (t, 1 H, J=4.6 Hz), 5.24 (d, 1 H, J=3.8 Hz), 6.10 (t, 1 H, J=6.6 Hz), 8.10 (s, 1 H), 9.43 (br s, 1 H), 11.56 (br s, 1 H); $^{13}C$ NMR (DMSO-d6) δ 18.61, 25.73, 27.73, 38.87, 40.20, 61.20, 70.38, 73.30, 84.77, 87.75, 93.06, 99.16, 116.19 ($CF_3$, $J_{C-F}$=288.9 Hz), 142.96, 149.68, 156.41 ($COCF_3$, $J_{C-F}$=36.4 Hz), 162.00; UV (MeOH) nm (e×$10^3$) 230 (11.9), 292 (12.3); IR (KBr) cm$^{-1}$ 3521, 3407, 3320, 2239, 1697, 1285, 1214, 1195, 1032; MS (FAB$^+$) m/z: 420 (MH$^+$), 330, 304; HRMS (FAB$^+$) calc. for $C_{17}H_{21}N_3O_6F_3$ 420.1382 (MH$^+$), found 420.1382; Anal. calc. for $C_{17}H_{20}N_3O_6F_3$: C, 48.69; H, 4.81; N, 10.02, found: C, 48.51; H, 4.73; N, 9.92.

B. Conversion of 5 to 5-(6-N-(trifluoroacetyl)-aminohexyl)-2'-deoxyuridine (6).

A mixture of 5 (480 mg, 1.14 mmol) and 10% Pd/C (95 mg) in MeOH (6 mL) was stirred under $H_2$ pressure (50 psi) at room temperature for 3 days. The mixture was filtered through celite and concentrated to give 6: 475 mg, 98% yield; mp 136°–140° C. ($Et_2O$); $^1H$ NMR (DMSO-d6) δ 1.2–1.3 (m, 4 H), 1.3–1.5 (m, 4 H), 2.07 (m 2 H), 2.16 (m, 2 H), 3.15 (t, 2 H, J=6.9 Hz), 3.56 (m, 2 H), 3.76 (m, 1 H), 4.23 (br s, 1 H), 5.02 (br s, 1 H), 5.23 (br s, 1 H), 6.16 (t, 1 H, J=6.8 Hz), 7.68 (s, 1 H), 9.39 (br s, 1 H), 11.22 (br s, 1 H); $^{13}$C NMR (DMSO-d6) δ 26.14, 26.44, 28.07, 28.40, 28.40, 39.56, 39.98, 61.49, 70.65, 84.10, 87.51, 113.76, 116.20 (CF$_3$, J$_{C-F}$=288.5 Hz), 136.33, 150.60, 156.33 (COCF$_3$, J$_{C-F}$=35.6 Hz), 163.68; UV (MeOH) nm (ex10$^3$) 212 (15.9), 268 (13.6); IR (KBr) cm$^{-1}$ 3552, 3384, 3328, 1701, 1684, 1559, 1203, 1180, 1170; MS (FAB$^+$) m/z: 424 (MH$^+$); HRMS (FAB$^+$) calc. for C$_{17}$H$_{25}$N$_3$O$_6$F$_3$ 424.1695 (MH$^+$), found 424.1706; Anal. calc. for C$_{17}$H$_{24}$N$_3$O$_6$F$_3$: C, 48.23; H, 5.71; N, 9.92, found: C, 48.19; H, 5.68; N, 10.00.

C. Conversion of 6 to 5-(6-N-(trifluoroacetyl)-aminohexyl)-5'-O-(4,4'-dimethoxytrityl)-2'-deoxyuridine (7).

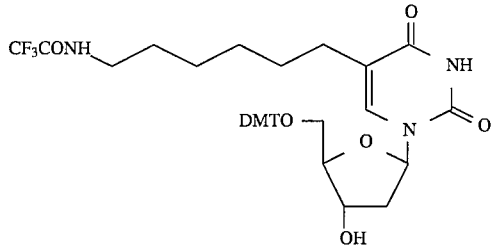

To a solution of 6 (490 mg, 1.16 mmol) in dry pyridine (10 mL) was added 4,4'-dimethoxytrityl chloride (430 mg, 1.27 mmol) in small portions over 30 min. at room temperature. The reaction mixture was stirred at room temperature for 2 h. The mixture was then concentrated, and the residue was purified by flash chromatography (SiO$_2$, MeOH (3–10%)/pyridine (0.5%)/CH$_2$Cl$_2$) to give 7: white amorphous solid, 753 mg, 89% yield; $^1$H NMR (CDCl$_3$) δ 1.0–1.1 (m, 4 H), 1.15–1.3 (m, 2 H), 1.3–1.4 (m, 2 H), 1.71 (m, 1 H), 1.93 (m, 1 H), 2.32 (m, 1 H), 2.41 (m, 1 H), 2.64 (br s, 1 H), 3.31 (dd, 1 H, J=2.4 Hz, 10.5 Hz), 3.38 (m, 2 H), 3.53 (dd, 1 H, J=2.6 Hz, 10.5 Hz), 3.79 (s, 6 H), 4.05 (1 H), 4.57 (m, 1 H), 6.44 (dd, 1 H, J=6.2 Hz, 7.5 Hz), 6.71 (br s, 1 H), 6.83 (d, 4 H, J=8.6 Hz), 7.2–7.5 (m, 7 H), 7.39 (2 H), 7.57 (s, 1 H), 9.22 (s, 1 H); $^{13}$C NMR (CDCl$_3$) δ 25.71, 26.40, 28.22, 28.32, 28.32, 39.90, 40.97, 55.27, 63.50, 72.44, 84.70, 86.39, 86.77, 113.27, 115.82, 115.97 (CF$_3$, J$_{C-F}$=287.4 Hz), 127.14, 127.98, 128.20, 130.11, 135.48, 135.90, 144.30, 150.75, 157.26 (COCF$_3$, J$_{C-F}$=36.8 Hz), 158.65, 164.10; UV (MeOH) nm (ex10$^3$) 234 (22.1), 270 (10.6); IR (KBr) cm$^{-1}$ 3329, 1701, 1680, 1508, 1252, 1178; MS (FAB$^+$) m/z: 726 (MH$^+$), 725 (M$^+$), 303; HRMS (FAB$^+$) calc. for C$_{38}$H$_{42}$N$_3$O$_8$F$_3$ 725.2924 (M$^+$), found 725.2964; Anal. calc. for C$_{38}$H$_{42}$N$_3$O$_8$F$_3$: C, 62.89; H, 5.83; N, 5.79, found: C, 62.65; H, 5.77; N, 6.05.

D. Conversion of 7 to 5-(6-N-(trifluoroacetyl)-aminohexyl)-5'-O-(4,4'-dimethoxytrityl)-2'-deoxyuridine 2-cyanoethyl N,N-diisopropylphosphoramidite (4).

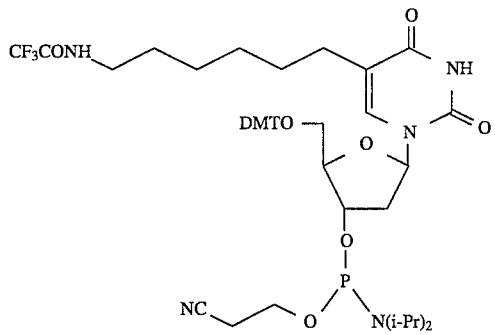

To a solution of 7 (300mg, 0.41 mmol) in CH$_2$Cl$_2$ (3.0 mL) was added diisopropylethylamine (0.216 mL, 1.24 mmol) and 2-cyanoethyl N,N-diisopropylchlorophosphine (0.120 mL, 0.54 mmol) successively at room temperature. The mixture was stirred for 1h, followed by dilution with 100 mL of CH$_2$Cl$_2$, extraction with 5% aq. NaHCO$_3$, drying over Na$_2$SO$_4$, and concentration. Purification by flash chromatography (SiO$_2$, EtOAc(30%)/Et$_3$N(1%)/CH$_2$Cl$_2$) gave phosphoramidite 4: 367mg as a mixture of two diastereomers, with a small amount of HPO(OCH$_2$CH$_2$CN)N(iPr)$_2$ as an inseparable impurity ($^{31}$P NMR δ 14.28), 88:12 of 4:H-phosphonate, yield of 4 93%; $^1$H NMR (CDCl$_3$) selected signals of diastereomers δ: 2.40 (t, 2 H, J=3.2 Hz, —OCH$_2$CH$_2$CN), 2.62 (t, 2 H, J=3.2 Hz, —OCH$_2$CH$_2$CN), 3.15 (m, 4 H, CF$_3$CONHCH$_2$—), 3.79 (s, 3 H, OMe), 3.80 (s, 3 H, OMe), 4.11 (m, 1 H, H$_4$·), 4.16 (m, 1 H, H$_4$·), 4.6–4.7 (m, 2 H, H$_3$·), 6.40 (m, 1 H, H$_1$·), 6.43 (m, 1 H, H$_1$·), 6.56 (m, 2 H, CF$_3$CONH—); $^{31}$P NMR (CDCl$_3$) δ: 148.57, 148.93; MS (FAB$^+$) m/z: 926 (MH$^+$), 818, 708, 404, 303; HRMS (FAB$^+$) calc. for C$_{47}$H$_{60}$N$_5$O$_9$F$_3$P 926.4081 (MH$^+$), found 926.4065.

Example 2

This example illustrates synthesis of 5-(3-N-(Trifluoroacetyl)-aminopropyl)-5'-O-(4,4'-dimethoxytrityl)-2'-deoxyuridine 2-cyanoethyl N,N-diisopropylphosphoramidite, 8, beginning with 5-iodo-2'-deoxyuridine.

A. Conversion of 5-iodo-2'-deoxyuridine to 5-(3-N-(Trifluoroacetyl)-amino-1-propynyl)-2'-deoxyuridine (9).

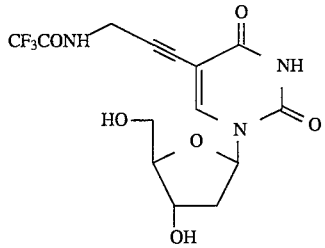

To a suspension of 5-iodo-2'-deoxyuridine (1.018 g, 2.82 mmol) in CH$_2$Cl$_2$ (14 mL) at 0° C. was added trifluoroacetic anhydride (3.98 mL, 28.24 mmol). The mixture was stirred at 0° C. for 2h and then at room temperature for 12 h. After concentration of the mixture, the residue was dried in vacuo at room temperature to give 3',5'-di-O-trifluoroacetyl-5-iodo-2'-deoxyuridine as a solid foam.

To a mixture of 3',5'-di-O-trifluoroacetyl-5-iodo-2'-deoxyuridine, N-trifluoroacetyl-1-amino-2-propyne (1.27 mL, 8.46 mmol), tetrakis(triphenylphosphine)palladium (0) (325 mg, 0.282 mmol), and copper (I) iodide (107 mg, 0.564 mmol) were added dry DMF (14 mL) and Et$_3$N (0.786 mL, 5.64 mmol). The mixture was stirred at room temperature for 21 h, and then concentrated under a vacuum. The residue was purified by flash chromatography (SiO$_2$, MeOH (10%)/CH$_2$Cl$_2$). The fraction containing the desired product was concentrated and treated with anion exchange resin (AG1X8, HCO$_3^-$, 2.4 g, 3.0 eq.) in 30 mL of 1/1, CH$_2$Cl$_2$/MeOH at room temperature for 30 min. Evaporation of the solvent gave 9 as a white solid, 747 mg, 70% yield; $^1$H NMR (DMSO-d6) δ 2.18 (m, 2 H), 3.1–3.3 (m, 2 H), 3.55 (m, 2 H), 3.78 (m, 1 H), 4.08 (m, 1 H), 5.07 (t, 1 H, J=5.0 Hz), 5.22 (d, 1 H, J=4.2 Hz), 6.09 (t, 1 H, J=6.6 Hz), 8.18 (s, 1 H), 9.9–10.1 (br s, 1 H), 11.5–11.7 (br s, 1 H); $^{13}$C NMR (DMSO-d6) δ 29.46, 40.12, 61.00, 70.21, 75.40, 84.82, 87.51, 87.67, 97.68, 115.81 (CF$_3$, J$_{C-F}$=288 Hz), 144.18, 149.44, 156.08 (COCF$_3$, J$_{C-F}$=37 Hz), 161.62; UV (H$_2$O) nm (ex10$^3$) 232 (4.15), 288 (4.53); IR (KBr) cm$^{-1}$ 3482, 2950, 1700, 1476, 1304, 1214, 1156, 1100; MS (FAB$^+$) m/z: 378 (MH$^+$), 262; HRMS (FAB$^+$) calc. for C$_{14}$H$_{15}$N$_3$O$_6$F$_3$ 378.0913 (MH$^+$), found 378.0898.

17

B. Conversion of 9 to 5-(3-N-(Trifluoroacetyl)-aminopropyl)-2'-deoxyuridine (10).

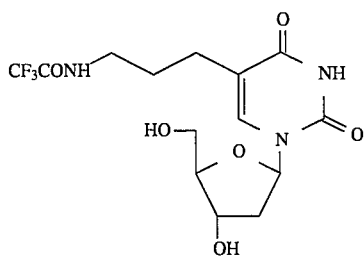

A mixture of 5-(3-N-(trifluoroacetyl)-amino-1-propynyl)-2'-deoxyuridine (9, 733 mg, 1.94 mmol) and 10% Pd/C (206 mg) in MeOH (25 mL) was stirred under $H_2$ pressure (50 psi) at room temperature for 3 days. The mixture was filtered through celite and concentrated to give the desired product, 10: 703 mg, 95% yield; mp 155°–158° C. ($CH_3CN$-hexane); $^1H$ NMR (DMSO-d6) δ 1.62 (m, 2 H), 2.08 (m, 2 H), 2.19 (m, 2 H), 3.16 (m, 2 H), 3.55 (m, 2 H), 3.75 (m, 1 H), 4.23 (br s, 1 H), 5.00 (br s, 1 H), 5.22 (br d, 1 H, J=2.8 Hz), 6.15 (t, 1 H, J=6.7 Hz), 7.67 (s, 1 H), 9.39 (br s, 1 H), 11.28 (br s, 1 H); $^{13}C$ NMR (DMSO-d6) δ 24.01, 27.31, 38.88, 39.63, 61.49, 70.61, 84.14, 87.50, 112.81, 116.16 ($CF_3$, $J_{C-F}$=288 Hz), 136.65, 150.50, 156.35 ($COCF_3$, $J_{C-F}$=36 Hz), 163.54; UV (MeOH) nm (ex10³) 268 (7.4); IR (KBr) cm⁻¹ 3432, 3320, 1734, 1696, 1654, 1274, 1204, 1185, 1153; MS ($FAB^+$) m/z: 382 ($MH^+$), 266; HRMS ($FAB^+$) calc. for $C_{14}H_{19}N_3O_6F_3$ 382.1226 ($MH^+$), found 382.1213; Anal. calc. for $C_{14}H_{18}N_3O_6F_3$: C, 44.10; H, 4.76; N, 11.02, found: C, 43.86; H, 4.77; N, 10.75.

C. Conversion of 10 to 5-(3-N-(Trifluoroacetyl)-aminopropyl)-5'-O-(4,4'-dimethoxytrityl)-2'-deoxyuridine (11).

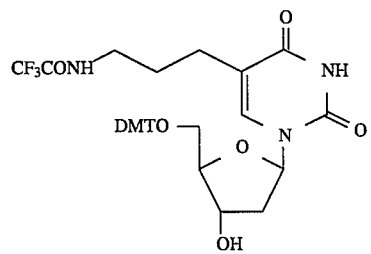

To a solution of 5-(3-N-(trifluoroacetyl)-aminopropyl)-2'-deoxyuridine (10, 100 mg, 0.262 mmol) in dry pyridine (2 mL) was added 4,4'-dimethoxytrityl chloride (90 mg, 0.266 mmol) at room temperature. The reaction mixture was stirred at room temperature for 3 h. The mixture was then concentrated, and the residue was purified by flash chromatography ($SiO_2$, MeOH (3–5%)/pyridine (0.5%)/$CH_2Cl_2$) to give the desired product, 11, as a white amorphous solid: 154 mg, 86% yield; $^1H$ NMR ($CDCl_3$) δ 1.35 (m, 2 H), 1.69 (m, 1 H), 1.87 (m, 1 H), 2.11 (br s, 1 H), 2.3–2.5 (m, 2 H), 3.06 (m, 2 H), 3.37 (m, 1 H), 3.55 (m, 1 H), 3.80 (s, 6 H), 4.06 (m, 1 H), 4.62 (m, 1 H), 6.44 (t, 1 H, J=6.7 Hz), 6.84 (d, 4 H, J=8.5 Hz), 7.2–7.4 (m, 10 H), 7.65 (s, 1 H), 8.5 (br s, 1 H); $^{13}C$ NMR ($CDCl_3$) δ 23.34, 28.10, 38.59, 40.99, 55.32, 63.59, 72.65, 84.92, 86.92, 86.98, 113.35, 114.09, 115.99 ($CF_3$, $J_{C-F}$=288 Hz), 127.36, 128.06, 128.29, 130.17, 130.23, 135.29, 137.41, 144.15, 150.56, 157.27 ($COCF_3$, $J_{C-F}$=37 Hz), 158.82, 164.62; UV (MeOH) nm (ex10³) 232 (19.2), 270 (9.2); IR (KBr) cm⁻¹ 3305, 1711, 1676, 1509, 1252, 1177; MS ($FAB^+$) m/z: 683 ($M^+$), 303; HRMS ($FAB^+$) calc. for $C_{35}H_{36}N_3O_8F_3$ 683.2455 ($M^+$), found 683.2437; Anal. calc. for $C_{35}H_{36}N_3O_8F_3$: C, 61.49; H, 5.31; N, 6.15, found: C, 61.17; H, 5.34; N, 5.85.

18

D. Conversion of 11 to 5-(3-N-(Trifluoroacetyl)-aminopropyl)-5'-O-(4,4'-dimethoxytrityl)-2'-deoxyuridine 2-cyanoethyl N,N-diisopropylphosphoramidite (8).

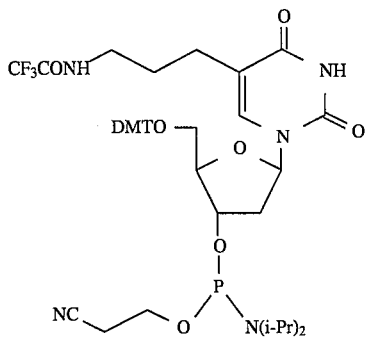

To a solution of 5-(3-N-(trifluoroacetyl)-aminopropyl)-5'-O-(4,4'-dimethoxytrityl)-2'-deoxyuridine (11, 190 mg, 0.278 mmol) in $CH_2Cl_2$ (3.0 mL) was added diisopropylethylamine (0.145 mL, 0.832 mmol) and 2-cyanoethyl N,N-diisopropylchlorophosphine (0.080 mL, 0.36 mmol) successively at room temperature. The mixture was stirred for 1 h, diluted with 100 mL of $CH_2Cl_2$, extracted with 5% aq. $NaHCO_3$, dried over $Na_2SO_4$, and concentrated. The residue was purified by flash chromatography ($SiO_2$, MeOH(3%)/$Et_3N$(1%)/$CH_2Cl_2$) to provide the desired phosphoramidite, 8, as a mixture of two diastereomers (264 mg), with a small amount of $HPO(OCH_2CH_2CN)N(iPr)_2$ as an inseparable impurity ($^{31}P$ NMR δ 14.28), 75:25 of phosphoramidite:H-phosphonate, yield of phosphoramidite: 99%; $^1H$ NMR ($CDCl_3$) selected signals of diastereomers δ: 1.6–1.7 (m, 2 H, $CF_3CONHCH_2CH_2CH_2$—), 1.8–1.9 (m, 2H, $CF_3CONHCH_2CH_2CH_2$—), 2.41 (t, 2 H, J=3.2 Hz, —$OCH_2CH_2CN$), 2.62 (t, 2 H, J=3.2 Hz, —$OCH_2CH_2CN$), 3.0–3.1 (m, 4 H, $CF_3CONHCH_2$—), 3.79 (s, 6 H, OMe), 3.80 (s, 6 H, OMe), 4.14 (m, 1 H, $H_4$, ), 4.29 (m, 1 H, $H_{4'}$), 4.7 (m, 2 H, $H_{3'}$), 6.40–6.48 (m, 2 H, $H_{1'}$), 7.64 (s, 1H, $H_{6'}$), 7.68 (s, 1 H, $H_6$); $^{31}P$ NMR ($CDCl_3$) δ: 148.66, 148.90; MS ($FAB^+$) m/z: 884 ($MH^+$), 666, 362, 303; HRMS ($FAB^+$) calc. for $C_{44}H_{54}N_5O_9F_3P$ 884.3611 ($MH^+$), found 884.3640.

Example 3

This example illustrates the synthesis of 5-(6-N-(trifluoroacetyl)-aminohexyl)-4-N-benzoyl-5'-O-(4,4'-dimethoxytrityl)-2'-deoxycytidine 2-cyanoethyl N,N-diisopropyl phosphoramidite, 12, beginning with commercially available 5-iodo-2'-deoxycytidine.

A. Conversion of 5-iodo-2'-deoxycytidine to 5-(6-N-(trifluoroacetyl)-amino-1-hexynyl)-2'-deoxycytidine (13).

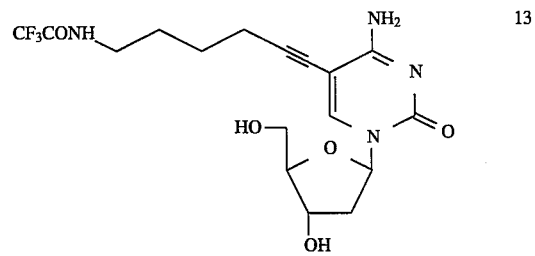

To 5-iodo-2'-deoxycytidine (1.496 g, 4.24 mmol), tetrakis(triphenylphosphine)palladium (0) (490 mg, 0.42 mmol), copper (I) iodide (163 mg, 0.86 mmol) and N-trifluoroacetyl-1-amino-5-hexyne (2.455 g, 12.7 mmol) were added DMF (21 mL) and $Et_3N$ (1.2 mL, 8.63 mmol). After stirring for 12 h, AG-1X8 anion exchange resin ($HCO_3^-$ form, 3.0 eq), 20 mL MeOH and 20 mL CH$_2$Cl$_2$ were added, and the suspension was stirred for 1 h. The reaction was filtered through a sintered glass funnel, and the DMF was removed in vacuo. Flash chromatography (SiO$_2$, MeOH (10%–20%)/CH$_2$Cl$_2$) provided 13: 1.389 g, 78% yield; mp 146°–148° C. dec. (EtOAc); $^1$H NMR (DMSO-d6) δ 1.55 (m, 4 H), 1.96 (m, 1 H), 2.11 (ddd, 1 H, J=3.5, 5.7, 13.0 Hz), 2.41 (t, 2 H, J=6.5 Hz), 3.20 (m, 2 H), 3.56 (m, 2 H), 3.77 (m, 1 H), 4.18 (m, 1 H), 5.03 (t, 1 H, J=5.0 Hz), 5.18 (d, 1 H, J=4.1 Hz), 6.10 (t, 1 H, J=6.5 Hz), 6.71 (br s, 1 H), 7.67 (br s, 1 H), 8.05 (s, 1 H), 9.42 (m, 1 H); $^{13}$C NMR (DMSO-d6) δ 18.67, 25.26, 27.61, 38.73, 40.73, 61.06, 70.18, 72.27, 85.26, 87.41, 90.40, 95.31, 115.99 (CF$_3$, J$_{C-F}$=288.6 Hz), 143.55, 153.52, 156.21 (COCF$_3$, J$_{C-F}$=35.6 Hz), 164.41; UV (H$_2$O) nm (ε×10$^3$) 298 (8.1), 236 (15.7), 208 (25.8); IR (KBr) cm$^{-1}$ 3441, 3275, 1706, 1636, 1506, 1176, 1094; MS (FAB$^+$) m/z: 419 (MH$^+$); HRMS (FAB$^+$) calc. for C$_{17}$H$_{22}$F$_3$N$_4$O$_5$ 419.1542 (MH$^+$), found 419.1558; Anal. calc. for C$_{17}$H$_{21}$F$_3$N$_4$O$_5$: C, 48.81; H, 5.06; N, 13.39, found: C, 48.46; H, 4.98; N, 13.32.

B. Conversion of 13 to 5-(6-N-(trifluoroacetyl)-aminohexyl)-2'-deoxycytidine (14).

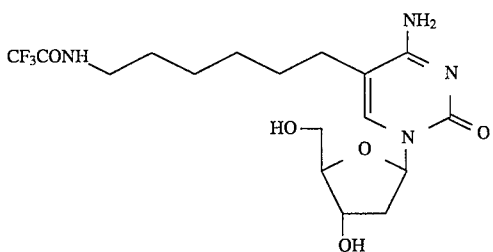

A mixture of 13 (1.379 g, 3.30 mmol) and 10% Pd/C (70 mg) in MeOH (6.6 mL) was stirred under H$_2$ pressure (50 psi). After 20 h the mixture was filtered through celite and concentrated. Flash chromatography (SiO$_2$, MeOH (20%)/CH$_2$Cl$_2$) gave 14: 1.235 g, 89% yield; mp 126°–129° C. (MeOH/CH$_3$CN); $^1$H NMR (DMSO-d6) δ 1.21–1.33 (m, 4 H), 1.33–1.52 (m, 4 H), 1.95 (m, 1 H), 2.06 (ddd, 1 H, J=3.3, 5.9, 13.0 Hz), 2.20 (t, 2 H, J=7.1 Hz), 3.15 (m, 2 H), 3.54 (m, 2 H), 3.74 (m, 1 H), 4.20 (m, 1 H), 4.97 (t, 1 H, J=5.0 Hz), 5.16 (d, 1 H, J=4.1 Hz), 6.15 (t, 1 H, J=6.7 Hz), 6.63–6.99 (br s, 1 H), 6.99–7.35 (br s, 1 H), 7.60 (s, 1 H), 9.38 (m, 1 H); $^{13}$C NMR (DMSO-d6) δ 26.01, 26.59, 27.77, 28.12, 28.24, 39.18, 40.32, 61.32, 70.39, 84.77, 87.12, 105.40, 118.28 (CF$_3$, J$_{C-F}$=288.4 Hz), 138.10, 154.91, 156.11 (COCF$_3$, J$_{C-F}$=35.6 Hz), 164.71; UV (H$_2$O) nm (ε×10$^3$) 280 (7.9); IR (KBr) cm$^{-1}$ 3423, 3309, 1713, 1668, 1615, 1493, 1187, 1155, 1101; MS (FAB$^+$) m/z 423 (MH$^+$); HRMS (FAB$^+$) calc. for C$_{17}$H$_{26}$F$_3$N$_4$O$_5$ 423.1855 (MH$^+$), found 423.1878; Anal. calc. for C$_{17}$H$_{25}$F$_3$N$_4$O$_5$: C, 48.34; H, 5.97; N, 13.26, found: C, 48.21; H, 5.77; N, 13.19.

C. Conversion of 14 to N4-benzoyl-5-(6-N-(trifluoroacetyl)-aminohexyl)-5'-O-(4,4'-dimethoxytrityl)-2'-deoxycytidine (15).

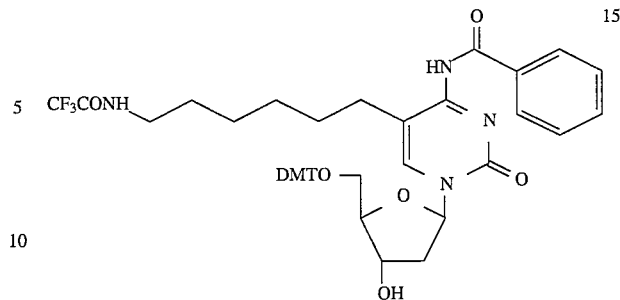

To a mixture of 14 (854 mg, 1.62 mmol) and 4,4'-dimethoxytrityl chloride (585 mg, 1.73 mmol) was added pyridine (15 mL). After stirring for 4 h, 80 mL of CH$_2$Cl$_2$ was added, the mixture was extracted with 5% Na$_2$CO$_3$, dried over Na$_2$SO$_4$, and concentrated. Flash chromatography (SiO$_2$, pyridine (1% )/MeOH (2% )/CH$_2$Cl$_2$) provided 15: 1.130 g, 84% yield: $^1$H NMR (CDCl$_3$) δ 1.00–1.18 (m, 4 H), 1.20–1.45 (m, 4 H), 1.94 (m, 1 H), 2.23 (m, 1 H), 2.34 (m, 1 H), 2.49 (ddd, 1 H, J=3.2, 5.6, 13.4 Hz), 3.16 (m, 2 H), 3.32 (dd, 1 H, J=2.3, 10.5 Hz), 3.58 (dd, 1 H, J=2.7, 10.5), 3.80 (s, 6 H), 4.07 (m, 1 H), 4.59 (m, 1 H), 6.25 (m, 1 H), 6.43 (t, 1 H, J=6.6 Hz), 6.85 (d, 4 H, J=7.7 Hz), 7.26–7.38 (m, 6 H), 7.38–7.48 (m, 5 H), 7.53 (m, 1 H), 7.76 (s, 1 H), 8.26 (d, 2 H, J=7.3 Hz), 13.1–13.6 (br s, 1 H); $^{13}$C NMR (CDCl$_3$) δ 26.06, 27.37, 28.45, 28.62, 28.77, 39.78, 41.23, 55.12, 63.17, 71.89, 85.16, 86.31, 86.60, 113.13, 115.74 (CF$_3$, J$_{C-F}$=287.9 Hz), 116.31, 126.98, 127.84, 127.98, 128.05, 129.61, 129.95, 132.36, 135.33, 136.94, 144.14, 147.87, 157.05 (COCF$_3$, J$_{C-F}$=36.6 Hz), 158.48, 159.32, 179.45; UV (MeOH) nm (ε×10$^3$) 332 (21.4), 268 (10.0), 236 (25.5); IR (KBr) cm$^{-1}$ 3331, 1709, 1567, 1509, 1252, 1176; MS (FAB$^+$) m/z 829 (MH$^+$); HRMS (FAB$^+$) calc. for C$_{45}$H$_{48}$F$_3$N$_4$O$_8$ 829.3424 (MH$^+$), found 829.3436; Anal. calc. for C$_{45}$H$_{47}$F$_3$N$_4$O$_8$: C, 65.21; H, 5.72; N, 6.76, found: C, 65.57; H, 5.80; N, 6.55.

D. Conversion of 15 to 5-(6-N-(trifluoroacetyl)-aminohexyl)-4-N-benzoyl-5'-O-(4,4'-dimethoxytrityl)-2'-deoxycytidine 2-cyanoethyl N,N-diisopropyl phosphoramidite (12).

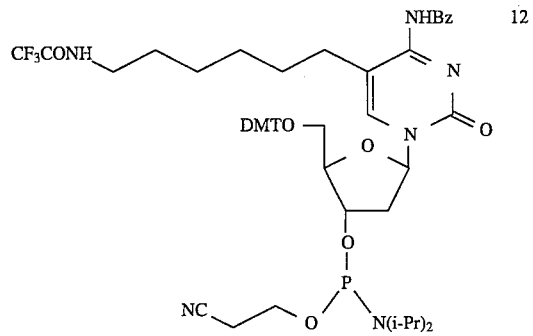

To a solution of 15 (917 mg, 1.11 mmol) in CH$_2$Cl$_2$ (10 mL) was added diisopropylethylamine (0.580 mL, 3.33 mmol) and 2-cyanoethyl N,N-diisopropylchlorophosphine (0.275 mL, 1.23 mmol). After 3 h, 50 mL CH$_2$Cl$_2$ was added. The mixture was extracted with saturated NaHCO$_3$, dried over Na$_2$SO$_4$, and then concentrated. Flash chromatography (SiO$_2$, pyridine (1%)/MeOH (1%)/CH$_2$Cl$_2$) gave 5: 944 mg, 83% yield; $^1$H NMR (CDCl$_3$) δ 1.00–1.10 (m, 7 H), 1.10–1.20 (m, 8 H), 1.20–1.40 (m, 5 H), 1.80–1.97 (m, 1 H), 2.17–2.30 (m, 1 H), 2.30–2.37 (m, 1 H), 2.39 (m, 1 H), 2.50–2.59 (m, 1 H), 2.62 (m, 1 H), 3.13 (m, 2 H), 3.21–3.32 (m, 1 H), 3.45–3.69 (m, 4 H), 3.69–3.90 (m, 7 H), 4.12–4.22 (m, 1 H), 4.62–4.73 (m, 1 H), 6.15–6.28 (br s, 1 H), 6.43 (m, 1 H), 6.80–6.90 (m, 4 H), 7.28–7.38 (m, 6 H), 7.38–7.48 (m, 5 H), 7.48–7.58 (m, 1 H), 7.75–7.83 (m, 1 H), 8.23–8.30 (m, 2 H), 13.20–13.50 (br s, 1 H); $^{13}$C NMR (CDCl$_3$) δ 20.12, 20.17, 20.37, 20.42, 24.41, 24.49, 24.55, 24.60, 26.12, 27.48, 28.55, 28.72, 28.75, 28.86, 39.84, 40.37, 43.10, 43.21, 43.31, 55.30, 57.97, 58.12, 58.27, 62.63, 62.79, 73.08, 73.20, 73.43, 73.57, 84.96, 85.07, 85.39, 85.43, 85.74, 85.76, 86.67, 113.23, 113.26, 115.82 (CF$_3$, J$_{C-F}$= 288.4 Hz), 116.37, 116.39, 117.32, 117.54, 127.13, 127.15, 127.96, 128.08, 128.21, 128.27, 129.78, 130.11, 132.39, 135.42, 136.75, 136.83, 137.23, 144.20, 147.77, 147.80, 155.73, 156.99 (COCF$_3$, J$_{C-F}$=37.1 Hz), 158.66, 159.39, 179.55; $^{31}$P (CDCl$_3$) δ 148.62, 149.12; MS (FAB$^+$) m/z 1029 (MH$^+$); HRMS (FAB$^+$) calc. for C$_{54}$H$_{65}$F$_3$N$_6$O$_9$P 1029.4503 (MH$^+$), found 1029.4551.

Example 4

This example illustrates the synthesis of various dodecanucleotides of the present invention.

DNA Synthesis

All oligodeoxynucleotides were synthesized trityl-on using a controlled pore glass solid support via the phosphite-triester method with an Applied Biosystems 391EP DNA synthesizer (1 μmol scale). For the synthesis of oligomers 16, 17 and 21, controlled pore glass support derivatized with 7 was prepared by standard methodology. For the synthesis of oligomer 18, the controlled pore glass support was derivatized with 11. Cleavage from the solid support and deprotection (except for the 5'-trityl group) was accomplished by treatment with concentrated NH$_4$OH for 15 hours at 55° C. The solution was then lyophilized with the addition of Et$_3$N every hour to inhibit detritylation. The residue was taken up in 1 mL of 100 mM triethylammonium acetate (TEAA), pH 7, and purified by reverse phase HPLC (Hamilton PRP-1, 300 mm×7 mm, Eppendorf CH-30 column heater, 60° C., 23–33% CH$_3$CN/100 mM TEAA, pH 7, 20 min., monitored at 260 nm). The fractions were lyophilized to dryness followed by repeated lyophilization to dryness with H$_2$O (2×1 mL) to remove any residual TEAA. Detritylation was accomplished by treatment with 80% AcOH (0.3 mL) for 20 min. After lyophilization with EtOH (0.3 mL), the residue was taken up in H$_2$O (1 mL), extracted with diethyl ether (3×1 mL) and then lyophilized to dryness. H$_2$O (1 mL) was added to the dry DNA pellet, and the solution quantified by UV absorbance at 260 nm at 70° C. The extinction coefficients (at 260 nm) of the natural nucleotides used for calculations were as follows: dAMP: 15,200; dCMP: 7,700; TMP: 8,830; dGMP: 11,500. The extinction coefficients of the unnatural nucleosides at 260 nm were determined to be the following: 5-(6-aminohexyl)-2'-deoxycytidine: 5,170 (prepared by hydrolysis of 15); 5-(6-aminohexyl)-2'-deoxyuridine: 9,200 (prepared by hydrolysis of 10). All oligonucleotide base compositions were confirmed by formic acid hydrolysis followed by HPLC analysis monitored at 260 nm or 270 nm (Alltech, HS, C-18; 20 mM K$_2$HPO$_4$, pH 5.6 (A), MeOH (B), 100% A to 40% B, 20 min.).

Dodecanucleotides 16–21 (Table I, SEQ ID NOS: 1–6 respectively) containing 1, 2, and 3 were prepared from appropriately protected phosphoramidites using an automated DNA synthesizer. All oligomers were characterized by digestion to constituent bases followed by HPLC analysis, 5'-end labeling followed by PAGE and also by laser desorption mass spectrometry. Data for the corresponding unmodified oligonucleotides 22 (SEQ ID NO: 7) and 23 (SEQ ID NO: 8) is provided for direct comparison.

TABLE I

| Oligodeoxynucleotide[a] | PAGE Mobility[b] | Laser Desorptions - MS | |
|---|---|---|---|
| | | Cal'd | Found |
| 16 5'-d(TTTTTTTTTTTT) | 15.5 | 3927 | 3925 |
| 17 5'-d(TTTTTTTTTTTT) | 4.4 | 4523 | 4520 |
| 18 5'-d(TTTTT̲T-T̲T-T̲T-T̲T-) | 16.3 | 3759 | 3756 |
| 19 5'-d(CTTTCTCTCCCT) | 16.6 | 3838 | 3841 |
| 20 5'-d(CTTTCTCTCCCT) | 16.2 | 3894 | 3892 |
| 21 5'-d(CTTTCTCTCCCT) | 3.8 | 4504 | 4509 |
| 22 5'-d(CTTTCTCTCCCT) | 21.9 | | |
| 23 5'-d(TTTTTTTTTTTT) | 20.8 | | |

[a]T̲, T̶ and C̲ correspond to zwitterionic monomers 1, 2 and 3 respectively.
[b]Polyacrylamide gel electrophoretic mobility is given in cm from the origin of the gel.
The samples were electrophoresed in a 20% polyacrylamide, 7 M urea denaturing gel using Tris-Borate-EDTA buffer at pH 8.5–9.0.

Example 5

This example provides the conditions for duplex formation and melting using the oligonucleotides 16–23.

Melting experiments

UV absorbance versus temperature profiles were measured on an HP 8452A diode-array UV spectrophotometer in a temperature controlled cell holder with an HP 89090A peltier temperature controller. The temperature of the cell holder was increased from 0° C. to 90° C. in 1° C. increments at a heating rate of 1°/min. The temperature of the solution was monitored by a thermocouple placed in the cell solution (10 mm path length only). N$_2$ gas (ice-cold) was passed over the cell at low temperatures to avoid the condensation of moisture. Experiments were performed a minimum of twice with different samples and T$_m$'s were averaged. Free energy values (in part) and melting temperatures were obtained by non-linear regression using a two-state model. An excellent fit of the experimental data was seen in all cases. Reverse melting experiments (90° C. to 0° C., 1°/min.) and reduced rate forward melting experiments (0° C. to 90° C., 0.5°/min.) were also performed, and found to give T$_m$'s within 0.5° C. Plots of 1/T$_m$ versus ln C$_T$ were used to obtain thermodynamic parameters. For the T$_m$ versus concentration studies, the following total oligonucleotide concentrations were employed: 140 μM, 70 μM, 46 μM, 28 μM, 18 μM, 12 μM, 8.0 μM, 5.0 μM. A 1.0 mm path length cell was used for 140 μM to 12 μM concentrations, and a 10 mm path length cell for 8.0 mM and 5.0 mM concentrations. Chimeric duplexes were formed between the modified oligonucleotides 16–21 and their complementary natural oligonucleotides by mixing 2.5 μM each of 16–21 with 2.5 μM of the complementary oligonucleotide (see Table II) in H$_2$O at pH 7 containing 10 mM sodium phosphate, 0.1 mM EDTA and the indicated concentration of NaCl. Natural duplexes were similarly formed between 22 and 23 and their complementary oligomers.

The duplex melting temperatures (under low ionic strength conditions, 50 mM NACl), free energies with complementary natural DNA under low (50 mM NACl) and high (1M NaCl) ionic strength conditions, and their duplex melting temperatures with mismatched natural DNA under low ionic strength conditions (50 mM NaCl) are summarized in Table II.

As Table II indicates, the modified oligonucleotides of the present invention, in the presence of complementary DNA, exhibit melting temperatures approximately equal to the corresponding natural oligomers 22 and 23. Additionally, the presence of positively charged ammonium moieties and the added steric bulk of the alkyl linking groups had no appreciable effect on the free energy of formation for any of the modified oligonucleotides 16–21. To ensure that all amino groups present in the duplexes are in their protonated form at pH 7, experiments were also conducted at pH 5.5 with essentially no change in the results.

TABLE II

| Oligo | $T_m$(C.°) | $T_m$(C.°) A-mismatch | $T_m$(C.°) G-mismatch | Free Energy of Formation $\Delta G°$ (Kcal/mol) 50 mM NaCl | 1 M NaCl |
|---|---|---|---|---|---|
| 16 | 21.5[a] | | | −3.5 | |
| 17 | 19.0[a] | | 13.5[c] | −3.6 | |
| 18 | 20.0[a] | | | −3.3 | |
| 19 | 39.1[b] | | 32.7[d] | −8.9 | −10.3 |
| 20 | 45.4[b] | 26.0[e] | | −10.6 | −12.7 |
| 21 | 41.5[b] | 21.0[e] | 36.9[d] | −9.4 | −9.4 |
| 22 | 39.4[b] | 20.9[e] | 32.0[d] | −9.1 | −12.5 |
| 23 | 22.5[a] | | 11.5[c] | −4.2 | |

[a]determined with 5'-d(A)$_{12}$ (SEQ ID NO: 9)
[b]determined with 5'-d(AGGGAGAGAAAG) (SEQ ID NO: 10)
[c]determined with 5'-d(AAAAGAAAAAAA) (SEQ ID NO: 11)
[d]determined with 5'-d(AGGGAGGGAAAG) (SEQ ID NO: 12)
[e]determined with 5'-d(AGGGAAAGAAAG) (SEQ ID NO: 13)

Example 6

This example illustrates the nuclease resistance of the modified oligonucleotides of the present invention.

Into an Eppendorf tube was placed 0.15 optical density units of fully zwitterionic oligomer 21 or natural oligomer 22, 0.03 units of snake venom phosphodiesterase, 0.48 units of bacterial alkaline phosphatase, 4 µL of 100 mM $MgCl_2$, 8 µL of 0.25M Tris-HCl (pH 8.1) and 10 µL of water for a total reaction volume of 40 µL. The mixture was incubated at 37° C. and aliquots were removed at 30 minute time intervals. The amount of oligomer degradation associated with each aliquot was determined by HPLC (Hamilton PRP-1, 300 mm×7 mm, monitored at 260 nm). Under these conditions, all of the natural oligomer 22 was consumed after 30 minutes, whereas the fully zwitterionic oligomer 21 was not completely degraded even after 2 hours.

The foregoing is offered primarily for purposes of illustration. It will be readily apparent to those skilled in the art that the structures, methods, composition components, syntheses and use conditions, and other parameters of the system described herein may be further modified or substituted in various ways without departing from the spirit and scope of the invention.

What is claimed is:

1. A modified oligonucleotide having the formula:

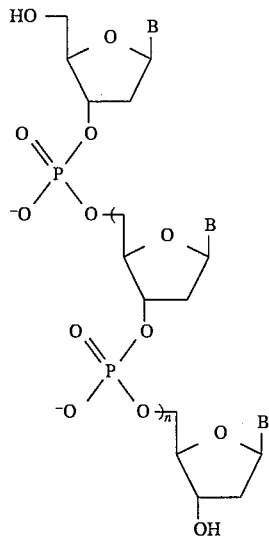

wherein n is an integer of from 4 to 30; and each B is a radical independently selected from the group consisting of,

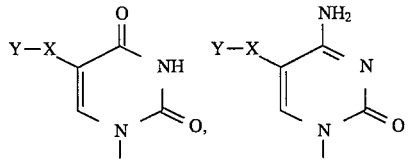

adenine, guanine, thymine and cytosine, wherein each X is a linking group independently selected from the group consisting of $C_1$–$C_{10}$ alkyl, $C_1$–$C_{10}$ unsaturated alkyl, dialkyl ether and dialkylthioether;

each Y is a cationic moiety independently selected from the group consisting of —$(NH_3)^+$, —$(NH_2R^1)^+$, —$(NHR^1R^2)^+$, and —$(NR^1R^2R^3)^+$; and $R^1$, $R^2$, and $R^3$ are each independently lower alkyl having from one to ten carbon atoms, with the proviso that when n is from 4 to 8, no more than 30% Bs are adenine, guanine, cytosine or thymine, and when n is from 9 to 30, no more than 50% Bs are adenine, guanine, cytosine or thymine, wherein said modified oligonucleotide forms chimetic duplexes when subjected to a complementary natural oliogonucleotide in $H_2O$ at pH 7 in the presence of 10 mM sodium phosphate, 0.1 mM EDTA and 50 mM sodium chloride.

2. The modified oligonucleotide of claim 1, wherein
n is an integer of from 4 to 15; and
each B is a radical independently selected from the group consisting of,

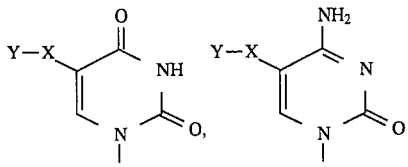

adenine, guanine, thymine and cytosine,
wherein
each X is a linking group independently selected from the group consisting of $C_1$–$C_{10}$ alkyl and $C_1$–$C_{10}$ unsaturated alkyl; and
each Y is a cationic moiety independently selected from the group consisting of —$(NH_3)^+$, —$(NH_2R^1)^+$, —$(NHR^1R^2)^+$, and —$(NR^1R^2R^3)^+$.

3. The modified oligonucleotide of claim 1, wherein n is 10 and each B is a radical independently selected from the group consisting of,

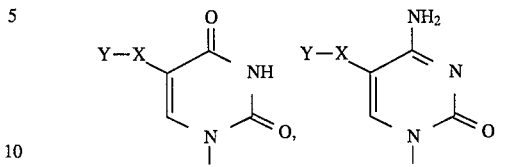

thymine and cytosine,
wherein
each X is a linking group independently selected from the group consisting of $C_3$–$C_6$ alkyl and $C_3$–$C_6$ unsaturated alkyl; and
each Y is —$(NH_3)^+$.

* * * * *